US00PP11281P

United States Patent [19]

Yamamoto

[11] Patent Number: Plant 11,281

[45] Date of Patent: Mar. 14, 2000

[54] DENDROBIUM PLANT NAMED 'SANOKKU'

[76] Inventor: Jiro Yamamoto, 1-12-30 Hamano, Okayama City, Okayama 700, Japan

[21] Appl. No.: 08/929,295

[22] Filed: Sep. 5, 1997

[51] Int. Cl.[7] ..... A01H 5/00

[52] U.S. Cl. ..... Plt./311

[58] Field of Search ..... Plt./311

[56] References Cited

PUBLICATIONS

Application for Registration of Species (Variety), No. 6407, filed Nov. 5, 1993 (J. Yamamoto, inventor)—copies in English and Japanese.

Certificate of Registration No. 5,835 for Registration Variety of Himezakura 'Sanokku' under Japanese Plants Variety Regulation Article 12, Item 4, No. 1, Nov. 14, 1997 (copies in English and Japanese).

GTITM UPOUROM Citation For 'Himezakura Sanokku' As Per JP PBR 6407, Nov. 5, 1993.

Sander'S List Of Orchid Hybrids Addendum 1991–1995; pp. 263, 286, 301, 315, 327, 329, 332, and 334.

*Primary Examiner*—Howard J. Locker
*Assistant Examiner*—Kent L. Bell
*Attorney, Agent, or Firm*—Banner & Witcoff, Ltd.

[57] ABSTRACT

A new and distinct variety of orchid, more particularly a Dendrobium hybrid cultivar plant, having durable, white flowers is disclosed. The plant's vigorous blooms make it particularly well suited as a small sized potted plant.

2 Drawing Sheets

DISCOVERY OF THE NEW VARIETY

The orchid of this application was discovered by the applicant in January 1991 as an outstanding member of a large population of seedlings obtained by crossing Dendrobium Oberon 'Princess' (unpatented) with Dendrobium Cassiope 'Sugiyama' (unpatented). Oberon is a cross between Dendrobium Sao Paulo and Dendrobium Star Carnival. Cassiope is a cross between *Dendrobium moniliforme* and *Dendrobium nobile*. These crosses have been registered with The Royal Horticultural Society of England. The mother plant, Dendrobium Oberon 'Princess', is a small variety with small but thick white flowers with lips of purplish violet and a small disc of maroon color in the lip. The father plant, Cassiope 'Sugiyama', has white flowers with a slight pink color, with a lip that is lightly pinkish purple at the center. The flower is small and blooms well, but lacks durability. These two varieties were cross-bred on Jan. 20, 1988, and their 150 seedlings were cultivated. The plant of the new variety was immediately recognizable in January 1991 as superior in its flowering and general growth habit to all other seedlings obtained from this cross.

When the first flowers of 'Sanokku' bloomed, in January 1991, the cane was 11 cm long, with seven nodes. Four of the nodes had eleven flowers. After the new variety had been observed for a period of time its other features of vigorous and early blooming were also noted. The next year two new pseudobulbs appeared. By 1993 the canes grew to be 25 cm, with eleven nodes. Out of these eleven nodes, nine had 31 flowers altogether. Some nodes had four flowers each. Thus, unaffected by the length of the canes, the flowers bloom well. If kept in a cool place, the plant will continue to bloom for over one month.

ASEXUAL REPRODUCTION

Since its discovery in January 1991 the variety has been grown in the applicant's greenhouse at Yamamoto Dendrobium Nursey, Hamano 1-12-30, Okayama City, Japan. During this time a number of plants of the new variety have been asexually reproduced, by the use of stem propagation, tissue culture, and by dividing the plants.

All of the propagations reproduced true to the original in both plant, flower and other characteristics, with no sign of mutation. All plants in the variety have continued to be readily distinguishable from both parents in flower quality, plant growth habit and other characteristics. The new variety has been designated as Dendrobium Himezakura 'Sanokku'.

DESCRIPTION OF THE PHOTOGRAPHS

The photographs show the colors of the new variety as nearly true as possible with illustrations of this type.

DESCRIPTION OF THE PLANT AND FLOWERS

Figure 1:
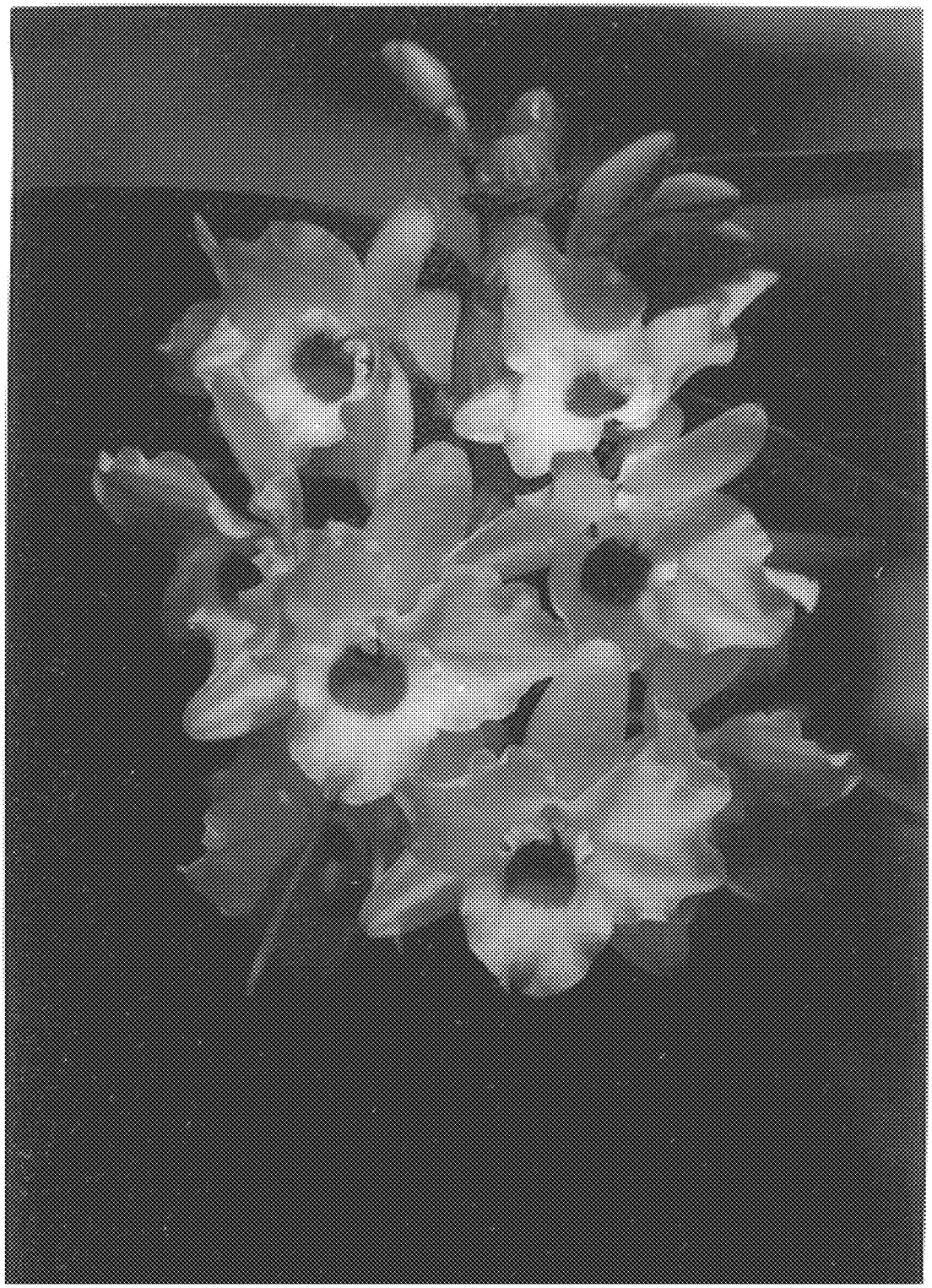
FIG. 1 is a closeup view of a spray of flowers typical of the new variety.
Figure 2:
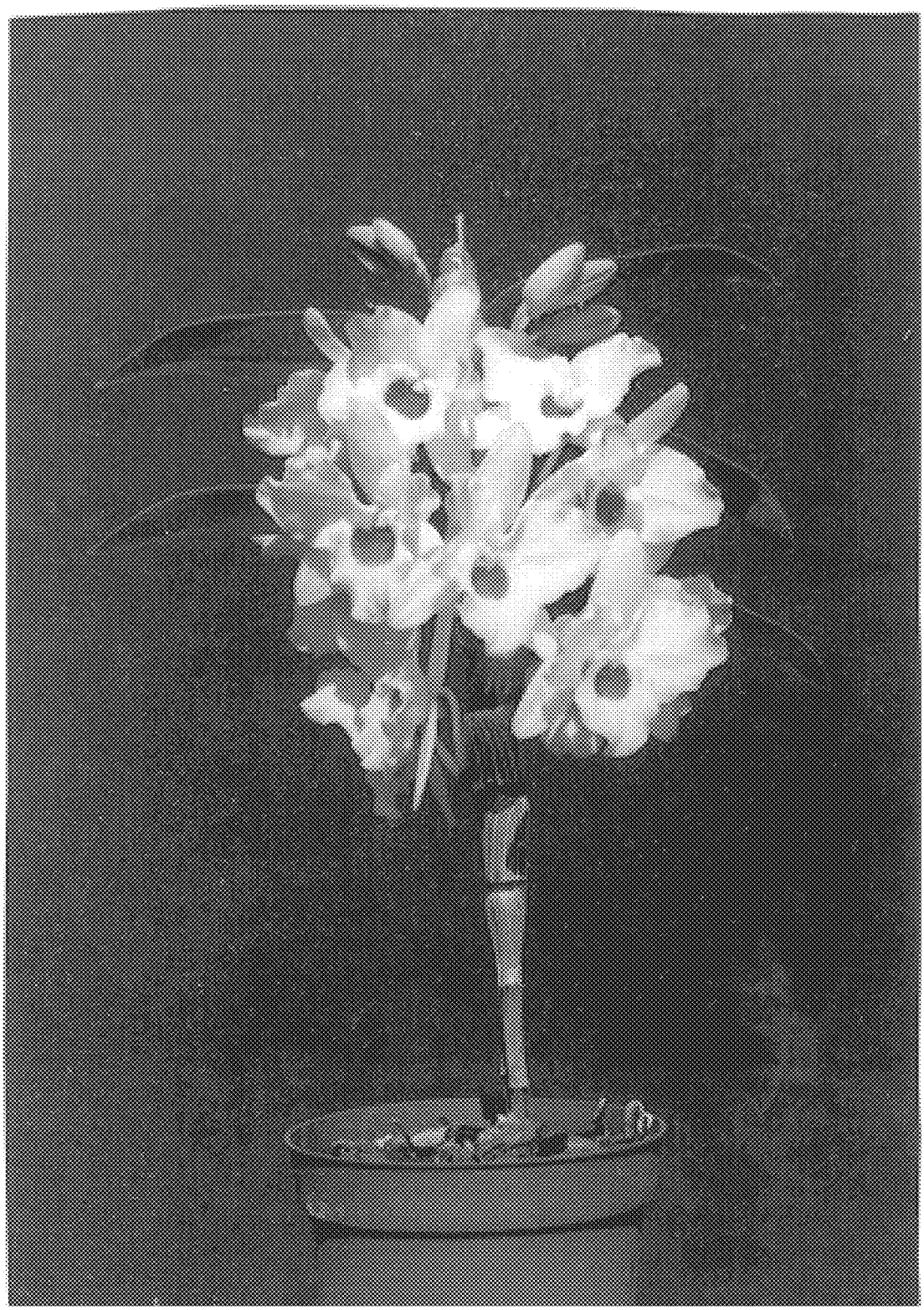
FIG. 2 shows the same flowers but is viewed from a greater distance to reveal the appearance of the flower spray and its relationship to the general size of the plant.

The plant with its flowers is illustrated in the color photographs accompanying this specification. The chart used in the identification of the colors is that of The Royal Horticultural Society (R.H.S. Colour Chart). The age of the pseudobulb on the plant described in 1–2 years.

The new variety 'Sanokku' has a number of features which suit it for use as a small potted plant. The cane is slightly thin but sturdy, with short internodes which cause the flowers to bloom in clusters. Three to four flowers grow on each node, compared with two to three flowers per node on the comparable variety, Dendrobium Snowflake 'Otome'. The flower of 'Otome' is white, with a soft pink color on the edge of the petals. The lip has a yellow color. This clustering makes the plant showy and enjoyable. The flowers often bloom on canes even shorter than 10 cm. The typical internode dimensions are 2.3 cm long and 1.7 cm wide at the top and 3.5 cm long and 1.5 cm wide at the bottom.

The flower diameter is 5.7 cm on average. The dorsal sepal, lateral sepals, and petals are all white except for a slight pale pinkish purple at the tip. On the lip is an evident dark pinkish purple eye suffusing from the basal portion towards the central portion of the lip. New blooms have a greenish cast around the eye, which later turns to a yellowish cream color. The shape of the petals is oval, with few waves at the edge. The petal is 2.3 cm wide and 3 cm long. The dorsal sepal and lateral sepals are elliptical in shape, with no waves on the edges. The sepals are 1.2 cm wide and 3 cm in length.

The new variety 'Sanokku' is a deciduous orchid. It is a small plant, with early blooming flowers which are much more durable than other small varieties of Dendrobiums. If forms excellent buds and its flowers last longer than those of its parents. This characteristic makes 'Sanokku' particularly well suited for forcing.

The plant can be cultivated by standard methods in any area if grown in a greenhouse or vinyl house with a heating system. If the greenhouse is kept at a temperature of over 17° C. at night, new pseudobulbs will appear and will be matured by the end of July. Within the winter of that same year to the following spring, buds can be seen on the new pseudobulbs. Buds can be small, medium, or large. Small buds are 1.4 cm long, 0.5 cm wide, and 144B in color. Medium buds are 1.7 cm long, 0.6 cm wide, and 144C in color. Large buds are 2.4 cm long, 1.0 cm wide, and 144D in color. The buds are oblong and their texture is firm. 'Sanokku' has the same characteristics as other standard Dendrobium types with respect to cold and heat endurance, as well as flowering period. Cut flowers last about one day. If refrigerated, they will keep about one week. Blooms on the plant last four to six weeks.

Specific features of the plant are listed below.

Size of plant: Typically 20–30 cm tall.
Plant posture: Erect.
Pseudobulb:
*Frontage.*—Narrow rectangular.
*Cross section.*—Irregular round.
*Height.*—20–35 cm.
*Diameter.*—11–20 mm.
*Color.*—144B.
Leaf:
*General shape.*—Linear ellipse.
*Shape of tip.*—Cuspidate.
*Vertical cross section.*—Almost flat.
*Direction of leaf.*—Horizontal.
*Length.*—10.8 cm.
*Width.*—4.1 cm.
*Foliage.*—Sessile.
*Base of foliage.*—Sheathed.
*Surface color.*—Green, 137B.
*Underside color.*—Light green, 146C.
*Thickness.*—0.6–1.0 mm.
*Variegation.*—None.
*Color of sheath.*—139C.
*Pubescence on leaf & sheath.*—None.
*Number of leaves.*—7–10 on largest pseudobulb stem.
Flowers:
*Arrangement.*—Raceme.
*Number of blooms per stem.*—3–5.
*Thickness of flower stem.*—1.1–2.0 mm.
*Length of flower stem.*—11–30 mm.
*Color of flower stem.*—145C.
*Direction of flower stem.*—Slanting upward.
*Size of bract leaf.*—2.3 cm long, 1.8 cm wide.
*Color of bract leaf.*—Light green, 148B.
*Single or double bloom.*—Single.
*Mode of bloom.*—Holding or flat.
*Length of spur.*—Less than 3 mm.
*Width of flower.*—41–60 mm.
*Vertical length of flower.*—41–60 mm.
*Dorsal sepal.*—Shape: Elliptical. Shape: Elliptical. Tip: Cuspidate. Degree of twist: None. Degree of curl: Flat. Waves at edges: None. Width: 11–15 mm. Length: 21–30 mm. Margin: Entire. Base: Sessile.
*Lateral sepals.*—Shape: Pointed elliptical. Tip: Cuspidate. Degree of twist: None. Direction of curl: Flat. Waves at edges: None. Width: 11–15 mm. Length: 21–30 mm. Margin: Entire. Base: Sessile.
*Petals.*—Shape: Rectangular. Tip: Obtuse. Degree of twist: None. Direction of curl: Flat. Waves at edges: Slight undulation. Cut at edges: Slight. Direction of leaf protrusion from stem: Perpendicular. Width: 21–30 mm. Length: 21–30 mm. Margin: entire. Base: sessile; mentum short, approximately 0.8 cm.
*Lip.*—Shape obouate: Elliptical. Cross section: Flat. Existence of twist: None. Waves at edges: Slight undulation. Cut at edges: Slight. Existence of pubescence: None. Appendage at base of flower: None. Width: 21–25 mm. Length: 21–30 mm. Margin: entire. Base: convolute.
*Color of total flower.*—White with light to dark pinkish purple, with cream around eye.
*Color of dorsal sepal.*—Inner side pattern: Single color, with a tinge of pinkish purple at the margins extending from the central portion to the tip. Inner side base color: 155B. Inner side pinkish purple: 77D. Outer side pattern: Single color, with a tinge of pinkish purple at the margins extending from the central portion to the tip. Outer side base color: 155B. Outer side pinkish purple: 77D.
*Color of lateral sepals.*—Inner side pattern: Blurred. Inner side base color: 155B. Inner side multicolor area: 77D. Outer side pattern: Blurred. Outer side base color: 155B. Outer side multicolor area: 77D.
*Petals.*—Inner side pattern: Blurred. Inner side base color: 155B. Inner side multicolor area: 77D. Outer side pattern: Blurred. Outer side base color: 155B. Outer side multicolor area: 77D.
*Lip.*—Inner side pattern: Dark pinkish purple eye suffusing from the basal portion towards the central portion of the lip, emerging into a greenish cream in new flowers, which later fades into a cream. Inner side base color: 155B. Inner side central eye: 78B. Outer side pattern: Blurred. Outer side base color: 155B. Outer side central eye: 75C.
*Column.—Inner side pattern: Single color. Inner side base color:* 144B. Outer side pattern: Single color. Outer side base color: 144B.
*Pollen color.*—155D.
*Fragance of flower.*—None.
*Bloom period.*—Early winter/winter/spring.
*Duration of bloom.*—30 days.
*Irregularity of flower form.*—None.
*Dropping of lip.*—None.
*Discoloring of lip.*—None.
*Cold and heat durability.*—Temperatures above freezing, up to 104° F.
*Resistance to disease.*—Average; exact durability unknown.
*Resistance to insects.*—Average; exact durability unknown.
*Development of offshoots.*—With too much nitrogen, offshoots emerge from the top of the cane instead of flowers; otherwise, offshoots emerge from the base of the plant.

I claim:

1. A new and distince orchid plant, as illustrated and described.

* * * * *